US008975054B2

(12) United States Patent
Samain

(10) Patent No.: US 8,975,054 B2
(45) Date of Patent: Mar. 10, 2015

(54) MICROORGANISIMS USED TO SYNTHESIZE OLIGOSACCHARIDES

(75) Inventor: Eric Samain, Gieres (FR)

(73) Assignee: Centre National de la Recherche Scientifique (CNRS), Paris (FR)

(*) Notice: Subject to any disclaimer, the term of this patent is extended or adjusted under 35 U.S.C. 154(b) by 585 days.

(21) Appl. No.: 12/723,264

(22) Filed: Mar. 12, 2010

(65) Prior Publication Data
US 2010/0267660 A1 Oct. 21, 2010

Related U.S. Application Data

(62) Division of application No. 11/447,287, filed on Jun. 6, 2006, now Pat. No. 7,820,422.

(60) Provisional application No. 60/690,837, filed on Jun. 16, 2005.

(51) Int. Cl.
*C12N 9/10* (2006.01)
*C12N 1/20* (2006.01)
*C12P 19/04* (2006.01)
*C12P 19/26* (2006.01)
*C12P 19/34* (2006.01)

(52) U.S. Cl.
CPC ............. *C12N 9/1081* (2013.01); *C12N 1/20* (2013.01); *C12P 19/04* (2013.01); *C12P 19/26* (2013.01); *C12P 19/34* (2013.01)
USPC ........... 435/193; 435/7.1; 435/320.1; 435/6.1

(58) Field of Classification Search
None
See application file for complete search history.

(56) References Cited

U.S. PATENT DOCUMENTS

| 4,935,349 | A | 6/1990 | McKnight |
| 6,255,076 | B1 | 7/2001 | Widner |
| 6,503,744 | B1 | 1/2003 | Gilbert |
| 6,709,834 | B2 | 3/2004 | Gilbert et al. |
| 6,770,475 | B1 | 8/2004 | Inoue |
| 2002/0042369 | A1 | 4/2002 | Gilbert |

FOREIGN PATENT DOCUMENTS

| WO | WO 92/16640 | | 10/1992 |
| WO | WO 01/04341 | A1 | 1/2001 |
| WO | WO 02/074942 | A2 | 9/2002 |

OTHER PUBLICATIONS

Whisstock et al.,( Q Rev Biophys. Aug. 2003; 36(3): 307-340).*
Office Action issued by the Examiner in U.S. Appl. No. 11/447,287 on Dec. 11, 2009.
Office Action issued by the Examiner in U.S. Appl. No. 11/447,287 on Dec. 10, 2008.
Office Action issued by the Examiner in U.S. Appl. No. 11/447,287 on Jun. 16, 2008.

Meyhack, B., et al., "Two yeast acid phosphatase structural genes are the result of a tandem duplication and show different degrees of homology in their promoter and coding sequences," The EMBO Journal, (1982), pp. 675-680, vol. 1, No. 6.
Varki, A., "Mini Review—Diversity in the sialic acids," Glycobiology, (1992), pp. 25-40, vol. 2, No. 1.
Castro-Palomino, J.C., et al., "Synthesis of Ganglioside GD3 and its Comparison with Bovine GD3 with Regard to Oligodendrocyte Apoptosis Mitochondrial Damage," Chem. Eur. J., (2001), pp. 2178-2184, vol. 7, No. 10.
Zeng, G., et al., "Suppression of Ganglioside GD3 Expression in a Rat F-11 Tumor Cell Line Reduces Tumor Growth, Angiogenesis, and Vascular Endothelial Growth Factor Production," Cancer Research, (2000), pp. 6670-6676, vol. 60.
Willison, H.J., et al., "Synthetic disialylgalactose immunoadsorbents deplete anti-GQ1b antibodies from autoimmune neuropathy sera," Brain, (2004), pp. 680-691, vol. 127.
Birklé, S., et al., "Role of tumor-associated gangliosides in cancer progression," Biochimie, (2003), pp. 455-463, vol. 85.
Michon, F., et al., "Conformational Differences between Linear $\alpha(2\rightarrow 8)$-Linked Homosialooligosaccharides and the Epitope of the Group B Meningococcal Polysaccharide," Biochemistry, (1987), pp. 8399-8405, vol. 26.
Fernández-Checa, J.C., "Redox regulation and signaling lipids in mitochondrial apoptosis," Biochemical and Biophysical Research Communications, (2003), pp. 471-479, vol. 304.
Antoine, T., et al., "Highly Efficient Biosynthesis of the Oligosaccharide Moiety of the GD3 Ganglioside by Using Metabolically Engineered *Escherichia coil*," Angew. Chem. Int. Ed., (2005), pp. 2-4, vol. 44.
Antoine, T., et al., "Large-Scale In Vivo Synthesis of the Carbohydrate Moieties of Gangliosides GM1 and GM2 by Metabolically Engineered *Escherichia coli*," ChemBioChem, (2003), pp. 406-412, vol. 4.
Altschul, S.F., et al., "Basic Local Alignment Search Tool," J. Mol. Biol, (1990), pp. 403-410, vol. 215.
Karlin, S., et al., "Applications and statistics for multiple high-scoring segments in molecular sequences," Proc. Natl. Acad. Sci. USA, (1993), pp. 5873-5877, vol. 90.
Kanamori, A., et al., "Deaminated Neuraminic Acid-rich Glycoprotein of Rainbow Trout Egg Vitelline Envelope," The Journal of Biological Chemistry, (1990), pp. 21811-21819, vol. 265, No. 35.
Needleman, S.B., et al., "A General Method Applicable to the Search for Similarities in the Amino Acid Sequence of Two Proteins," J. Mol. Biol., (1970), pp. 443-453, vol. 48.
Gilbert, M., et al., "Biosynthesis of Ganglioside Mimics in *Campylobacter jejuni* OH4384," The Journal of Biological Chemistry, (2000), pp. 3896-3906, vol. 275, No. 6.
Nakayama, J., et al., "Expression Cloning of a Human $G_{T3}$ Synthase," The Journal of Biological Chemistry, (1996), pp. 3684-3691, vol. 271, No. 7.

(Continued)

*Primary Examiner* — Hope Robinson
(74) *Attorney, Agent, or Firm* — Foley & Lardner LLP

(57) ABSTRACT

The present invention relates to the enzymatic synthesis of oligosaccharides, particularly, sialylated oligosaccharides comprising the carbohydrate moeities of the gangliosides GM3, GD3, and GT3.

9 Claims, 3 Drawing Sheets

(56) References Cited

OTHER PUBLICATIONS

Russell, D.W., et al., "Nucleotide Sequence of the Yeast Alcohol Dehydrogenase II Gene," The Journal of Biological Chemistry, (1983), pp. 2674-2682, vol. 258, No. 4.

Ruf, P., et al., "Two New Trifunctional Antibodies for the Therapy of Human Malignant Melanoma," Int. J. Cancer, (2004), pp. 725-732, vol. 108.

Gilbert, M., et al., "Cloning of the Lipooligosaccharide α-2,3-Sialyltransferase from the Bacterial Pathogens *Neisseria meningitidis* and *Neisseria gonorrhoeae*," The Journal of Biological Chemistry, (1996), pp. 28271-28276, vol. 271, No. 45.

Cousens, L.S., et al., "High level expression of proinsulin in the yeast, *Saccharomyces cerevisiae*," Gene, (1987), pp. 265-275, vol. 61.

Colell, A., et al., "Ganglioside GD3 enhances apoptosis by suppressing the nuclear factor-κB-dependent survival pathway," The FASEB Journal, (2001), pp. 1068-1070, vol. 15.

Vieira, J., et al., "The pUC plasmids, an M13mp7-derived system for insertion mutagenesis and sequencing with synthetic universal primers," Gene, (1982), pp. 259-268, vol. 19.

McKnight, G.L., et al., "Identification and molecular analysis of a third *Aspergillus nidulans* alcohol dehydrogenase gene," The EMBO Journal, (1985), pp. 2093-2099, vol. 4, No. 8.

Johnston, M., et al., "Sequences That Regulate the Divergent GAL1-GAL10 Promoter in *Saccharomyces cerevisiae*," Molecular and Cellular Biology, (1984), pp. 1440-1448, vol. 4, No. 8.

Herskowitz, I., et al., "Control of Cell Type in *Saccharomyces cerevisiae*: Mating Type and Mating-type Interconversion," (1982), in the Molecular Biology of the yeast *Saccharomyces* (eds. Strathem, Jones and Broach) Cold Spring Harbor Lab., NY, pp. 181-209.

Nadano, D., et al., "A Naturally Occurring Deaminated Neuraminic Acid, 3-Deoxy-D-*glycero*-D-*galacto*-nonulosonic Acid (KDN)," The Journal of Biological Chemistry, (1986), pp. 11550-11557, vol. 261, No. 25.

Letinic, K., et al., "Letter to Neuroscience—C-Pathway Polysialogangliosides are Transiently Expressed in the Human Cerebrum During Fetal Development," Neuroscience. (1998), pp. 1-6, vol. 86, No. 1.

Altschul, S.F., et al., "Gapped Blast and PSI-Blast: a new generation of protein database search programs," Nucleic Acids Research, (1997), pp. 3389-3402, vol. 25, No. 17.

Pearson, W.R., et al., "Improved tools for biological sequence comparision," Proc.. Natl. Acad. Sci. USA, (1988), pp. 2444-2448, vol. 85.

Priem, B., et al., "A new fermentation process allows large-scale production of human milk oligosaccharides by metabolically engineered bacteria," Glycobiology, (2002), pp. 235-240, vol. 12, No. 4.

Henikoff, S., et al., "Amino acid substitution matrices from protein blocks," Proc. Natl. Acad. Sci. USA, (1992), pp. 10915-10919, vol. 89.

Samain, E., et al., "Gram-scale synthesis of recombinant chitooligosaccharides in *Escherichia coli*," Carbohydrate Research, (1997) pp. 35-42, vol. 302.

* cited by examiner

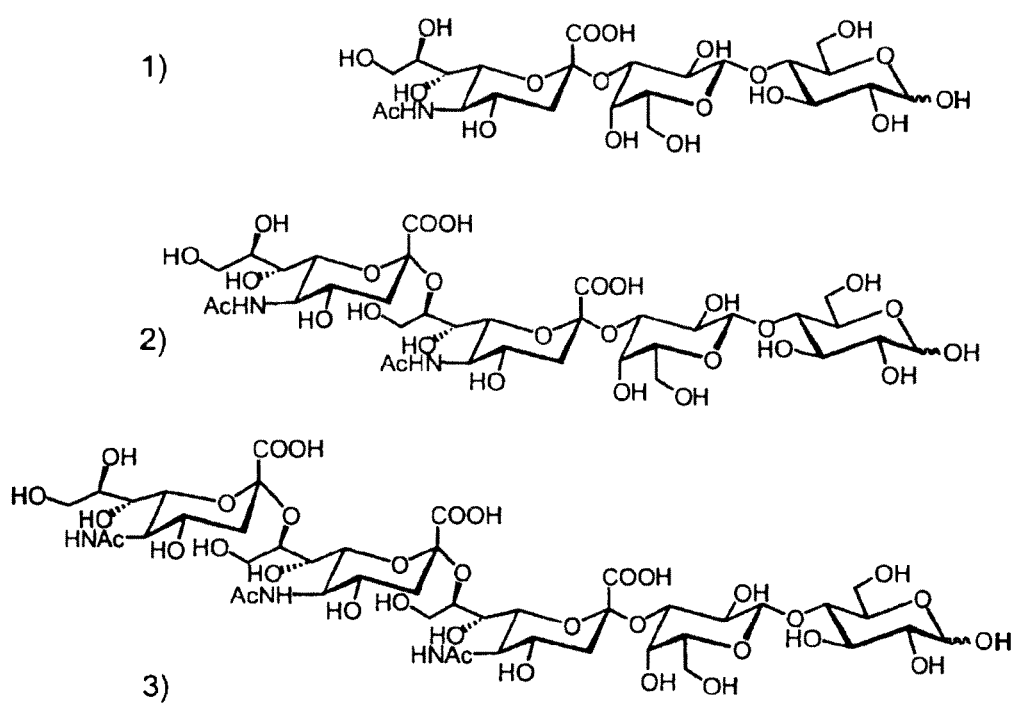
*Figure 3.* Structure of 1) II³(Neu5Ac)₂-lac 2) II³(Neu5Ac)₂-lac and 3) II³(Neu5Ac)₃-lac

MICROORGANISIMS USED TO SYNTHESIZE OLIGOSACCHARIDES

CROSS-REFERENCE TO RELATED PATENT APPLICATIONS

This application is a Divisional of U.S. Pat. No. 7,820,422, filed Jun. 6, 2006, now U.S. Pat. No. 7,820,422 incorporated herein by reference in its entirety, which claims priority from Provisional Application US Application 60/690,837, filed Jun. 16, 2005, incorporated herein by reference in its entirety.

FIELD OF THE INVENTION

The present invention relates to the enzymatic synthesis of oligosaccharides, particularly, sialylated oligosaccharides comprising the carbohydrate moeities of the gangliosides GM3, GD3, and GT3.

BACKGROUND OF THE INVENTION

It is now well-established that oligosaccharides play an important biological role especially as regards to the activity and function of proteins; thus, they serve to modulate the half-life of proteins, and occasionally they are involved in the structure of the protein. Oligosaccharides play an essential role in antigen variability (for example blood groups), and in certain bacterial infections such as those caused by *Neisseria meningitidis*.

As oligosaccharides are usually obtained in a low yield by purification starting from natural sources, the synthesis of oligosaccharides has become a major challenge of carbohydrate chemistry. In particular, it is a goal to supply sufficient amounts of well-characterized oligosaccharides, required for fundamental research or for any other potential applications.

The synthesis of complex oligosaccharides of biological interest may be performed chemically, enzymatically or microbiologically. Despite the development of new chemical methods for synthesizing oligosaccharides in the course of the last 20 years, the chemical synthesis of oligosaccharides remains very difficult on account of the numerous selective protection and deprotection steps, the lability of the glycoside linkages, the difficulties in obtaining regiospecific couplings, and the low production yields.

GD3 (Neu5Acα-8Neu5Acα-3Galβ-4GlcCer) is a minor ganglioside found in most normal tissues in higher vertebrates including humans. The GD3 level has been shown to increase during some pathological situations, such as cancers (glioma, melanoma) and to have an important role in tumor angiogenesis Zeng, et al. *Cancer Res*, 60:6670 (2000). Anti-GD3 monoclonal antibodies have been shown to inhibit the growth of human melanoma cells both in vitro and in vivo (Birkle, et al. *Biochimie*, 85, 455 (2003); Ruf, et al. *Int J Cancer*, 108, 725 (2004)). In normal cells, GD3 is a cell death effector, activating the mitochondrial-dependent apoptosome in response to apoptotic stimuli (Fernandez-Checa, *Biochem Biophys Res Commun*, 304, 471 (2003)). In addition, GD3 has a proapoptotic function by suppressing the nuclear factor-Kb-dependent survival pathway (Colell, et al. *Faseb J*, 15, 1068 (2001)).

Chemical synthesis of the oligosaccharide moiety of gangliosides is difficult to achieve (Castro-Palomino et al., *Chemistry*, 7, 2178 (2001)) but new efficient biotechnological techniques have recently been developed for the synthesis of GM3, GM2 and GM1 oligosaccharides (Priem et al. *Glycobiology*, 12, 235 (2002) and Antoine et al., *Chembiochem*, 4, 406 (2003)). The GM3 oligosaccharide (Neu5Acα-3Galβ-4Glc) was synthesized by a metabolically engineered *Escherichia coli* strain which overexpressed the *Neisseria meningitidis* genes for α-3 sialyltransferase and CMP-Neu5Ac synthase. Lactose and neuraminic acid (Neu5Ac) were supplied as exogenous precursors and actively internalized by *E. coli*'s β-galactosidase and Neu5Ac permease. To prevent catabolism of the precursors, a mutant strain devoid of both β-galactosidase and Neu5Ac aldolase activities was used.

Despite advances in the art, new biosynthetic methods for producing desired oligosaccharides are needed. The present invention addresses these and other needs.

BRIEF SUMMARY OF THE INVENTION

The present invention provides methods of producing oligosaccharides by fermentative growth of microorganisms. In particular, the invention relates to a method of synthesis of the oligosaccharide moieties of gangliosides selected from:

```
GM3  (Neu5Acα-3Galβ-4Glc),

GD3  (Neu5Acα-8Neu5Acα-3Galβ-4Glc),
and

GT3  (Neu5Acα-8Neu5Acα-8Neu5Acα-3Galβ-4Glc)
``` using bifunctional *Campylobacter jejuni* CstII sialyltransferases.

This method may be extended to the production of GM3, GD3 and GT3 by reacting the above oligosaccharide moities with ceramide.

DESCRIPTION OF THE DRAWINGS

FIG. 3 shows the structures of GM3 ($II^3(Neu5Ac)$-lac, 1); GD3 ($II^3(Neu5Ac)_2$-lac, 2) GT3 ($II^3(Neu5Ac)_3$-lac, 3).

DETAILED DESCRIPTION OF THE INVENTION

Introduction

Figure 1:
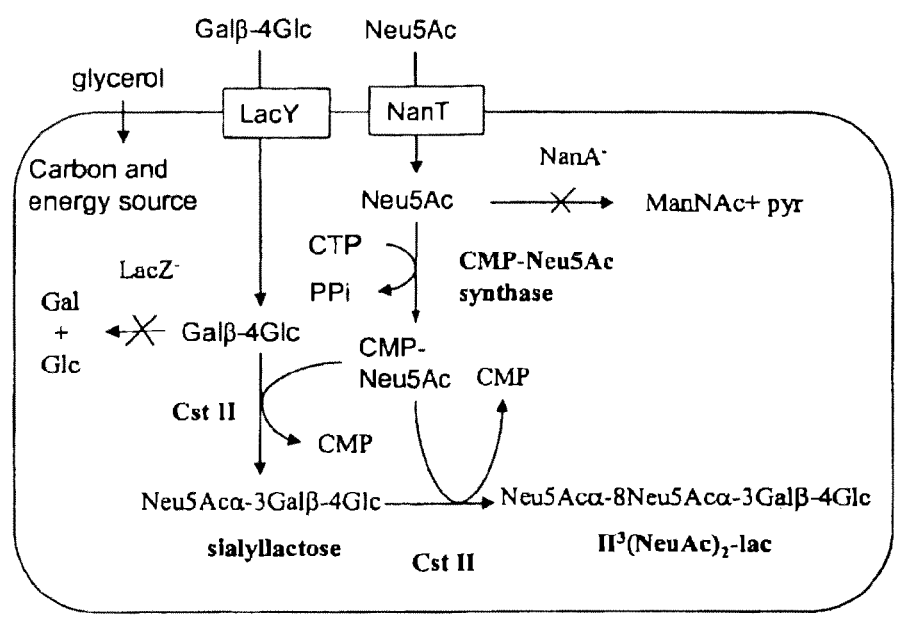
FIG. 1 shows the metabolically engineered pathway of $II^3(Neu5Ac)_2lac$ (GD3) biosynthesis in *Escherichia coli* K12. Lactose and Neu5Ac, which were internalized by the specific permeases LacY and NanT, could not be degraded because of β-galactosidase (LacZ) and aldolase (NanA) inactivation. Neu5Ac was converted into a nucleotide activated form (CMP-Neu5Ac) by CMP-Neu5Ac synthase and then transferred onto lactose by the α-3 sialyltransferase activity of CstII to form sialyllactose. A second Neu5Ac was transferred onto the first sialic acid by the α-8 sialyltransferase activity of CstII to form $II^3(Neu5Ac)_2lac$. CTP, cytidine triphosphate; PPi, inorganic pyrophosphate FIG. 2 show a production of oligosaccharides in a high-cell density culture of strain TA 15. The arrow indicates the start of induction and the addition of lactose (3 mM) and Neu5Ac (6 mM): (Δ) cell growth; (X) lactose, (◊) Neu5Ac; (●) $II^3(Neu5Ac)$-lac (1); (■) $II^3(Neu5Ac)_2$-lac (2); (♦) $II^3(Neu5Ac)_3$-lac (3); (○) sum of $II^3(Neu5Ac)$-lac, $II^3(Neu5Ac)_2$-lac and $II^3(Neu5Ac)_3$-lac. Concentrations are given in mM.

The present invention provides cell-based methods for enzymatically synthesizing sialylated oligosaccharides. Also provided are reaction mixtures, expression cassettes, and recombinant cells that are useful in methods for synthesizing sialylated oligosaccharides. Typically, the cells are grown in a medium that includes the precursors lactose and Neu5Ac.

Production of the sialylated oligosaccharides occurs during fermentative growth of the cells, as the precursors are taken up by the cells and metabolized to form the desired oligosaccharides, i.e., GM3, GD3 or GT3 oligosaccharides.

The methods of the invention rely on the general approach disclosed in WO 01/04341, an English translation of which is NZ516808. In general, the sialylated product saccharides are produced by growing a microorganism that comprises an enzymatic system for synthesizing an activated sialic acid (e.g., a CMP-sialic acid synthase polypeptide) and a bifunctional C. jejuni CstII sialyltransferase in the presence of a precursor of sialic acid and lactose, under conditions such that an activated sialic acid molecule is synthesized and transfer of the sialic acid moiety from the activated sialic acid molecule is catalyzed by the sialyltransferase to produce the sialylated product saccharide. Also provided by the invention are recombinant cells that can be used in the methods, as well as reaction mixtures that include the recombinant cells and are useful for producing the product sugars.

The nomenclature and general laboratory procedures required to practice the present invention are well known to those of skill in the art. These procedures can be found, for example, in Sambrook, et al., *Molecular Cloning: A Laboratory Manual* (2nd Ed.), Vol. 1-3, Cold Spring Harbor Laboratory, Cold Spring Harbor, N.Y., 1989.

DEFINITIONS

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, N.Y. (1992)). The synthesis and use of sialic acid compounds in a sialylation procedure is disclosed in international application WO 92/16640, published Oct. 1, 1992.

The term "bifunctional *Campylobacter jejuni* CstII sialyltransferase" refers to a sialyltransferase which exhibits both α2-3 and α2-8 sialyltransferase activities. In some embodiments, the CstII sialyltransferase from ATCC Accession No. 43438 is used.

An "acceptor substrate" or an "acceptor saccharide" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. For example, an acceptor substrate for the sialyltransferases used in the methods of the invention is lactose Galβ1,4-Glc.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for sialyltransferases used in the methods of the invention is CMP-Neu5Ac.

A "culture medium" refers to any liquid, semi-solid or solid media that can be used to support the growth of a microorganism used in the methods of the invention. In some embodiments, the microorganism is a bacteria, e.g., *E. coli*. Media for growing microorganisms are well known, see, e.g., Sambrook et al. and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel). Media can be rich media, e.g., Luria broth or terrific broth, or synthetic or semi-synthetic medium, e.g., M9 medium. In some preferred embodiments the growth medium comprises lactose and sialic acid.

"Commercial scale" refers to gram scale production of a sialylated product saccharide in a single reaction. In preferred embodiments, commercial scale refers to production of greater than about 50, 75, 80, 90 or 100, 125, 150, 175, or 200 grams.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

A "heterologous polynucleotide" or a "heterologous gene", as used herein, is one that originates from a source foreign to the particular host cell, or, if from the same source, is modified from its original form. Thus, a heterologous sialyltransferase gene in a cell includes a gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used. Transcription termination signals, enhancers, and other nucleic acid sequences that influence gene expression, can also be included in an expression cassette. When more than one heterologous protein is expressed in a microorganism, the genes encoding the proteins can be expressed on a single expression cassette or on multiple expression cassettes that are compatible and can be maintained in the same cell. As used herein, expression cassette also encompasses nucleic acid constructs that are inserted into the chromosome of the host microorganism. Those of skill are aware that insertion of a nucleic acid into a chromosome can occur, e.g., by homologous recombination. An expression cassette can be constructed for production of more than one protein. The proteins can be regulated by a single promoter sequence, as for example, an operon. Or multiple proteins can be encoded by nucleic acids with individual promoters and ribosome binding sites.

The term "isolated" refers to material that is substantially or essentially free from components which interfere with the activity biological molecule. For cells, saccharides, nucleic acids, and polypeptides of the invention, the term "isolated" refers to material that is substantially or essentially free from components which normally accompany the material as found in its native state. Typically, isolated saccharides, oligosaccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligosaccharides, e.g., sialylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are BLAST® and BLAST® 2.0 algorithms, which are described in Altschul et al. (1990) J. Mol. Biol. 215: 403-410 and Altschuel et al., (1977) Nucleic Acids Res. 25: 3389-3402, respectively. Software for performing BLAST® analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T, and X determine the sensitivity and speed of the alignment. The BLASTN program (for nucleotide sequences) uses as defaults a wordlength (W) of 11, an expectation (E) of 10, $M=5$, $N=-4$, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST® algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST® algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode the enzymes are preferably optimized for expression in a particular host cell (e.g., yeast, mammalian, plant, fungal, and the like) used to produce the enzymes.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) *Proteins*, W.H. Freeman and Company.

Bifunctional Sialyltransferases and Accessory Enzymes

As noted above, bifunctional sialyltransferases are used in the methods of the invention. Nucleic acids encoding such enzymes have been isolated from C. jejuni and are disclosed in U.S. Pat. Nos. 6,699,705 and 6,503,744 and WO/02074942, Exemplary *C. jejuni* strains which can be used as sources of bifunctional sialyltransferases include OH4384 (nucleic acid sequences are found in GENBANK® accessions AR271700 and AX934425), OH4382, O:10 (nucleic acid sequences are found in GENBANK® accessions AR271701 (SEQ ID NO: 1) AX934427 (SEQ ID NO: 2), O:23, and O:41 (nucleic acid sequences are found in GENBANK® accessions AR271702 (SEQ ID NO: 3) and AX934429 (SEQ ID NO: 4)). It shall be understood that conservatively modified variations as defined above of SEQ ID NOs: 1, 2, 3 and 4 may be applied herein.

Glycosyltransferase reactions require a nucleotide sugar which serves as sugar donor. Enzymes that are involved in synthesis of a nucleotide sugar or synthesis of the sugar are also called accessory enzymes. Accessory enzymes include those enzymes that are involved in the formation of a nucleotide sugar.

The sialyltransferases used in the methods of the invention require a CMP-sialic acid molecule, i.e., an activated sialic acid molecule, to serve as a donor of a sialic acid moiety. In some embodiments, the recombinant cells of the invention can naturally produce the CMP-sialic acid molecule that serves as a sugar donor for the sialyltransferase produced by the cell, as well as the nucleotide to which the sialic acid moiety is attached. However, some cells do not naturally produce sufficient amounts of either or both of the CMP or the sialic acid to produce the desired quantities of product saccharide In such situations, the recombinant cells of the invention can contain at least one heterologous gene that encodes an accessory enzyme, involved in synthesis of CMP-sialic acid.

Thus in some embodiment of the invention, a gene that encodes a CMP-sialic acid synthetase (EC 2.7.7.43, CMP-N-acetylneuraminic acid synthetase) is introduced into the cell. Sources for such genes are well known to those of skill in the art. In some preferred embodiments, the gene for CMP-sialic acid synthase from *Neisseria meningitis* MC58 is used (see e.g., Gilbert et al. (1996) *J. Biol. Chem.*, 271:28271-28276 and WO 01/04341).

Host Cells

The recombinant cells of the invention are generally made by creating or otherwise obtaining a polynucleotide that encodes the particular enzyme(s) of interest, placing the polynucleotide in an expression cassette under the control of a promoter and other appropriate control signals, and introducing the expression cassette into a cell. More than one of the enzymes can be expressed in the same host cells using a variety of methods. For example, a single extrachromosomal vector can include multiple expression cassettes or more that one compatible extrachromosomal vector can be used maintain an expression cassette in a host cell. Expression cassettes can also be inserted into a host cell chromosome, using methods known to those of skill in the art. Those of skill will recognize that combinations of expression cassettes in extra-chromosomal vectors and expression cassettes inserted into a host cell chromosome can also be used. Other modification of the host cell, described in detail below, can be performed to enhance production of the desired oligosaccharide. For example, the microorganism may be LacY+ and NanT+ allowing active transport of lactose and sialylic acid.

The recombinant cells of the invention are generally microorganisms, such as, for example, yeast cells, bacterial cells, or fungal cells. Examples of suitable cells include, for example, *Azotobacter* sp. (e.g., *A. vinelandii*), *Pseudomonas* sp., *Rhizobium* sp., *Erwinia* sp., *Bacillus* sp., *Streptomyces* sp., *Escherichia* sp. (e.g., *E. coli*), and *Klebsiella* sp., among many others. The cells can be of any of several genera, including *Saccharomyces* (e.g., *S. cerevisiae*), *Candida* (e.g., *C. utilis, C. parapsilosis. C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debaryomyces* (e.g., *D. subglobosus, D. cantarellii, D. globosus, D. hanseniii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*).

Promoters for use in *E. coli* include the T7, trp, or lambda promoters. A ribosome binding site and preferably a transcription termination signal are also provided. For expression of heterologous proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*. Methods of transforming prokaryotes other than *E. coli* are well known. For example, methods of transforming *Bacillus* species and promoters that can be used to express proteins are taught in U.S. Pat. No. 6,255,076 and No. 6,770,475.

In yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene*

61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

In some embodiments, the polynucleotides are placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter. A particularly preferred inducible promoter for expression in prokaryotes is a dual promoter that includes a tac promoter component linked to a promoter component obtained from a gene or genes that encode enzymes involved in galactose metabolism (e.g., a promoter from a UDP galactose 4-epimerase gene (galE)).

Inducible promoters for other organisms are also well known to those of skill in the art. These include, for example, the arabinose promoter, the lacZ promoter, the metallothionein promoter, and the heat shock promoter, as well as many others.

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to construct the cells of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the target cell. A number of selectable markers are known to those of skill in the art and are described for instance in Sambrook et al., supra. A preferred selectable marker for use in bacterial cells is a kanamycin resistance marker (Vieira and Messing, *Gene* 19: 259 (1982)). Use of kanamycin selection is advantageous over, for example, ampicillin selection because ampicillin is quickly degraded by β-lactamase in culture medium, thus removing selective pressure and allowing the culture to become overgrown with cells that do not contain the vector.

Construction of suitable vectors containing one or more of the above listed components employs standard ligation techniques as described in the references cited above. Isolated plasmids or DNA fragments are cleaved, tailored, and religated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill.

A variety of common vectors suitable for constructing the recombinant cells of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2.

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

In some embodiments, production of oligosaccharides is enhanced by manipulation of the host microorganism. For example, in *E. coli*, break down of sialic acid can be minimized by using a host strain that has diminished CMP-sialic acid synthase activity (NanA-). In *E. coli*, CMP-sialic acid synthase appears to be a catabolic enzyme. Diminishing the sialic acid degradative pathway in a host cell can be accomplished by disrupting the N-acetylneuraminate lyase gene (NanA, Accession number AE000402 region 70-963). Introduction of a sialyltransferase gene into these mutant strains results in a recombinant cell that is capable of producing large amounts of a sialylated product saccharide.

In some embodiments, the microorganisms are manipulated to enhance transport of an acceptor saccharide into the cell. For example, where lactose is the acceptor saccharide, *E. coli* cells that express or overexpress the LacY permease can be used. Also in *E. coli*, when lactose is the acceptor saccharide or an intermediate in synthesizing the sialylated product, lactose breakdown can be minimized by using host cells that are LacZ-.

Methods for Producing Product Saccharides

The invention also provides methods in which the host cells are used to prepare product sialylated oligosaccharides. The culture medium then includes lactose, sialic acid and possibly other precursors to donor substrates or acceptor substrates.

Those of skill will recognize that culture medium for microorganisms can be e.g., rich mediums, such as Luria broth, animal free Luria broth, or Terrific broth or synthetic medium or semi-synthetic medium, such as M9 medium.

Other components of the growth medium include the acceptor saccharide, lactose and sialic acid. Concentrations of the acceptor saccharide can be between 1 and 100 mM. In a preferred embodiment, the acceptor saccharide concentration is about 3 mM. Sialic acid can be present at a concentration between 1 and 100 mM, usually about 6 mM. In one preferred embodiment, Neu5Ac is present at or continuously supplied to maintain a concentration between 2 mM and 60 mM, such as about 6 mM, in the cell culture medium. Also, lactose is present at or continuously supplied to maintain a concentration between 1 mM and 30 mM, such as about 3 mM.

The methods of the invention can be used for producing sialylated oligosaccharides that are labeled with or enriched in radioisotopes; such oligosaccharides are extremely useful for fundamental biological or conformational analysis studies. The invention thus relates to a method for producing an oligosaccharide that is labeled with at least one radioisotope. In these embodiments, the culture medium includes substrates labeled said radioisotope and/or in the presence of a said precursor labeled with said radioisotope. The radioisotopes are preferably chosen from the group composed of: 14C, 13C, 3H, 35S, 32p, 33p.

The methods of the invention can also be used to activated oligosaccharides that may be used for the chemical synthesis of glycoconjugates or glycopolymers. The lactose acceptor can thus be modified such that glucose residue is replaced with an allyl group, said precursor now being allyl-I3-D galactoside rather than lactose. For example, the double bond of the allyl group is chemically modified by addition, oxidation or ozonolysis reactions.

Methods and culture media for growth of microorganisms are well known to those of skill in the art. Culture can be conducted in, for example, aerated spinner or shaking culture, or, more preferably, in a fermentor.

The products produced by the above processes can be used without purification. However, it is usually preferred to recover the product. Standard, well known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein.

Therapeutic and Other Uses

Sialylated oligosaccharides made according to the invention are useful in a wide range of therapeutic and diagnostic applications. They may be used, for example, as an agent for blocking cell surface receptors in the treatment of a host of diseases. As noted above, the oligosaccharides used for the chemical synthesis of glycoconjugates (e.g., glycolipids) or glycopolymers. The oligosaccharides or the glycoconjugates may be used, for example, as nutritional supplements, antibacterial agents, anti-metastatic agents and anti-inflammatory agents. The invention thus relates to an oligosaccharide according to the invention as a medicinal product in which the sialylated oligosaccharide or glycoconjugate is used to prepare a pharmaceutical composition. Methods for preparing pharmaceutical compositions are well known in the art.

For example, immunoadsorbents made with the trisaccharide Neu5Acα-8Neu5Acα-3Gal have recently been shown to deplete anti-GQ1b antibodies in autoimmune neuropathy sera from patients suffering from the Miller Fisher syndrome (Willison et al. *Brain*, 127, 680 (2004)). The large scale preparation of the GD3 oligosaccharide using the present invention is thus useful in the preparation of pharmaceutical composition in immunoadsorption therapies for the treatment of this syndrome. Therefore, the invention also contemplates a method for treating patients suffering from the Miller Fisher syndrome comprising depleting anti-GQ1b antibodies in sera from said patients using immunoadsorption with the large scale preparation of the oligosaccharide obtained according the method as defined above.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Figure 2:
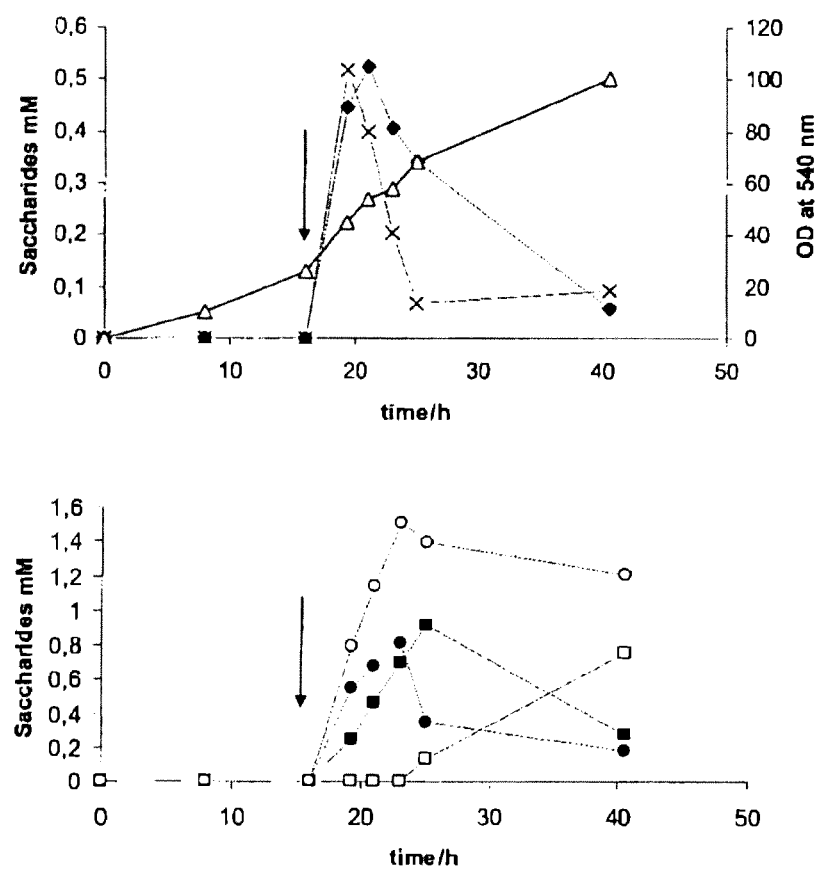

The metabolically engineered pathway for the biosynthesis of the GD3 oligosaccharide is described in FIG. 1 (see also Antoine et al. *Angew. Chem. Int. Ed.* 44:2-4 (2005)). The host strain, JM107nanA⁻, was an *Escherichia coli* K12 JM107 strain derivative in which the Neu5Ac aldolase activity was abolished by inactivating the nanA gene (Antoine et al. *Chembiochem*, 4, 406 (2003)). The cstII gene was amplified by PCR using the genomic DNA of *C. jejuni* (ATCC 43438) as template and cloned into a pUC18 plasmid to yield pUC-cstII. The $II^3(Neu5Ac)_2$lac production strain TA15 was constructed by transforming the host strain JM107nanA⁻ with two compatible plasmids: pUC18-cstII and pBBnsy (Priem et al. *Glycobiology*, 12, 235 (2002)) which was pBBR1-MCS1 derivative carrying the *N. meningitidis* gene for CMP-Neu5Ac synthase. The strain TA15 was cultured to high cell density with glycerol as the carbon source as previously described (Priem et al., supra). Lactose (3 mM) and Neu5Ac (6 mM) were added at the beginning of the fed-batch phase, as well as IPTG, which was the inducer of the Plac promoter of the two plasmids. The oligosaccharide content in the intracellular fraction of samples withdrawn at different cultivation times was analysed by HPAEC-PAD analysis (Supporting information FIG. S1). Lactose and Neu5Ac transiently accumulated in the intracellular fraction and were entirely consumed after 7 and 24 hours of incubation respectively (FIG. 2). Concurrently two compounds 1 and 2, putatively $II^3$(Neu5Ac)lac and $II^3(Neu5Ac)_2$lac, were produced, reaching their maximal concentrations 7 and 9 hours after induction, respectively. Concentrations of compounds 1 and 2 then decreased during the final stage of culture and this decrease correlated with the appearance of compound 3 which had a longer retention time in HPAEC (supporting information FIG. S1) and which was supposedly believed to be $II^3$(Neu5Ac)₃-lac. The structure of compounds 1, 2, 3 was confirmed by NMR and mass spectrometry of purified products. The $^{13}$C assignments of 1 and 2 (supporting information table S1, spectrum A) were in close agreement with previously described data (Gilbert, et al. *J Biol Chem*, 275, 3896 (2000)). $^{13}$C assignment of 3 was made by crosschecking $^{13}$C NMR spectrum of compound 2 and of α-8 linked tri-Neu5Ac F. Michon, et al. *Biochemistry*, 26, 8399 (1987)) (supporting information table S1, spectra B and C). In the positive mode, mass spectroscopic analysis showed the presence of quasi molecular ions [M+Na]⁺ at m/z 656 and [(M+Na—H)+Na]⁺ at m/z 678 in the spectrum of compound 1 and quasi molecular ions [M+Na]⁺ at ink 969 and [(M+Na—H)+Na]⁺ at m/z 991 in the spectrum of compound 2. The mass spectrum of compound 3 showed one peak at m/z 1304 in the positive mode corresponding to the quasi molecular ion [(M+3Na-3H)+Na]⁺ and one peak at m/z 1258 in the negative mode corresponding to the quasi molecular ion [(M+2Na-2H)—H]⁻. The structures of the carbohydrate moieties of the gangliosides GM3 ($II^3$(Neu5Ac)-lac) (1), GD3 ($II^3(Neu5Ac)_2$-lac) (2) and GT3 ($II^3(Neu5Ac)_3$-lac) (3) are presented in FIG. 3.

The formation of compound 3 can be explained by a side activity of the CstII sialyltransferase which would be able to add a third Neu5Ac onto the Neu5Ac of $II^3(Neu5Ac)_2$-lac. The production of compound 3 was somewhat unexpected because no such trisialylated structure has been described in the lipooligosaccharides of *C. jejuni* and there is no report of Cst-II being able to use a Neu5Acα-8Neu5Acα-3 motif as an acceptor. However in other species, such as humans, polysialogangliosides are synthesized by a single enzyme, GD3/GT3 synthase (Nakayama et al. *J Biol Chem,* 271, 3684 (1996)). GT3 is the precursor of C series gangliosides which are the major constituents in adult fish brain and are found abundantly in fetal brains of higher vertebrates (Letinic, et al. *Neuroscience,* 86, 1 (1998)). They are also found in various neuroectodermal tumors and there is thus potentially great interest in having easy access to the GT3 oligosaccharide.

By varying the lactose and NeuAc initial concentrations on one hand, and the culture time on the other, it is possible to favor either the production of GD3 or GT3 oligosaccharides. In our culture conditions the maximal production yields of GD3 (0.83 g·L$^{-1}$) and GT3 (0.91 g·L$^{-1}$) oligosaccharides were observed 9 hours and 24 hours after induction respectively. The yields of purified products were much lower due to the many purification steps. The purification procedure has thus to be considerably improved if these compounds were to be used in applications which require large quantities of material.

The cstII gene was amplified by PCR from *C. jejuni* ATCC43438 genome with the Pfu Turbo DNA polymerase from Stratagene. A ribosome binding site (RBS) was inserted upstream of the original start codon in the forward primer. The PCR product was cloned into pCR4Blunt-TOPO (Invitrogen) and subcloned into the EcoRI-PstI sites of pBluescript II KS (stratagene).

Sugars were quantified by high-performance anion-exchange chromatography (HPAEC) with a decade detector equipped with a carbopac PA10 column (DIONEX). Purified compounds 1, 2 and 3 were used as standards. The elution program consisted of a linear gradient of sodium acetate from 0 to 0.5 M in 45 minutes with an isocratic background of sodium hydroxide (100 mM). The flow rate was 0.8 mL/h.

Compounds 1 and 2 were purified from one liter of a strain TA15 culture harvested 9 hours after induction. The intracellular oligosaccharides were extracted from the cells and adsorbed on activated charcoal as previously described (Samain et al. *Carbohydr Res,* 302, 35 (1997)). They were then separated by size exclusion chromatography on a Biogel P6 column (4×100 cm) with NaNO$_3$ (50 mM) as the eluent and a flow rate of 45 ml h$^{-1}$ (supporting information FIG. S2). After desalting on a TSK HW40F/50F column (50×2, 1 cm) with water as the mobile phase and a flow rate of 4 ml min$^{-1}$, the yields of pure compounds 1 and 2 were 49 mg and 98 mg respectively.

Compound 3 was purified from one liter of a strain TA15 culture harvested 24 hours after induction. The procedure was the same as for compounds 1 and 2 except that complete purification required an additional High Performance Liquid Chromatography step on an ion exchange SP250/10 nucleosil column (10×1 cm). NaNO$_3$ (150 mM) was used as the eluent and the flow rate was 4 ml min$^{-1}$. After a last desalting step on a TSK HW40F/50F column, the final yield of pure compound 3 was 15 mg.

ESI mass spectra were recorded on a ZQ Waters micromass spectrometer (capillary 3.5 kV, cone voltage 80V). The 1D NMR spectra of II$^3$(Neu5Ac)lac and II$^3$(Neu5Ac)$_2$lac were recorded on a Bruker AVANCE 300 spectrometer as previously described (Antoine et al. *Chembiochem,* 4, 406 (2003)).

It is understood that the examples and embodiments described herein are for illustrative purposes only and that various modifications or changes in light thereof will be suggested to persons skilled in the art and are to be included within the spirit and purview of this application and scope of the appended claims. All publications (including GENBANK® accessions), patents, and patent applications cited herein are hereby incorporated by reference in their entirety for all purposes.

What is claimed is:

1. An *Escherichia coli* microorganism comprising a heterologous gene encoding a bifunctional *Campylobacter jejuni* sialyltransferase polypeptide that catalyzes the transfer of a sialyl moiety from an activated sialic acid molecule to lactose to form Neu5Acα-3Galβ-4Glc, wherein the *Escherichia coli* microorganism lacks Neu5Ac aldolase activity and β galactosidase activity, and wherein the heterologous gene encoding a bifunctional *Campylobacter jejuni* sialyltransferase has at least 95% sequence identity to a sequence selected from the group consisting of SEQ ID NOs: 1, 2, 3, and 4, and wherein the microorganism is LacY+ and NanT+ allowing active transport of lactose and sialylic acid.

2. A cell culture medium comprising lactose and Neu5Ac wherein the Neu5Ac is present at or continuously supplied to maintain a concentration between 2 mM and 60 mM, and an *Escherichia coli* microorganism comprising a heterologous gene encoding a bifunctional *Campylobacter jejuni* sialyltransferase polypeptide that catalyzes the transfer of a sialyl moiety from an activated sialic acid molecule to lactose to form Neu5Acα-3Galβ-4Glc, wherein the microorganism lacks Neu5Ac aldolase activity and β galactosidase activity, and wherein the heterologous gene encoding a bifunctional *Campylobacter jejuni* sialyltransferase has at least 95% sequence identity to a sequence selected from SEQ ID NOs: 1, 2, 3 and 4.

3. The cell culture medium of claim 2, wherein the lactose is present at or continuously supplied to maintain a concentration between 1 mM and 30 mM.

4. The *Escherichia coli* microorganism of claim 1, which further comprises a heterologous gene encoding a cytidine monophospho-(CMP)-sialic acid synthetase.

5. The *Escherichia coli* microorganism of claim 4, wherein the heterologous gene encoding the CMP-sialic acid synthetase is the gene for CMP-sialic acid synthetase from *Neisseria meningitis*.

6. The *Escherichia coli* microorganism of claim 1, wherein the heterologous gene encoding a bifunctional *Campylobacter jejuni* sialyltransferase is selected from the group consisting of SEQ ID NOs: 1, 2, 3, and 4.

7. The *Escherichia coli* microorganism of claim 1, wherein the heterologous gene encoding a bifunctional *Campylo-* bacter jejuni sialyltransferase is selected from the group consisting of SEQ ID NOs: 1, 2, 3, 4, and any conservative substitution of a nucleotide of SEQ ID NOs: 1, 2, 3 or 4.

8. The cell culture medium of claim 2, wherein the Neu5Ac is present at or continuously supplied to maintain a concentration of about 6 mM.

9. The cell culture medium of claim 3, wherein the lactose is present at or continuously supplied to maintain a concentration of about 3 mM.

* * * * *

SEQUENCE LISTING

```
<160> NUMBER OF SEQ ID NOS: 4

<210> SEQ ID NO 1
<211> LENGTH: 876
<212> TYPE: DNA
<213> ORGANISM: Campylobacter Jejuni
<220> FEATURE:
<223> OTHER INFORMATION: Campylobacter glycosyltransferases (NCBI
      accession number AR271701)

<400> SEQUENCE: 1
atgaaaaaag ttattattgc tggaaatgga ccaagtttaa aagaaattga ttattcaagg      60
ctaccaaatg attttgatgt atttagatgc aatcaattt attttgaaga taaatactat     120
cttggtaaaa aattcaaagc agtattttac aatcctggtc ttttttttga acaatactac     180
actttaaaac atttaatcca aaatcaagaa tatgagaccg aactaattat gtgttctaat     240
tacaaccaag ctcatctaga aaatgaaaat tttgtaaaaa cttttacga ttattttcct     300 gatgctcatt tgggatatga ttttttttaaa caacttaaag aatttaatgc ttattttaaa     360
tttcacgaaa tttatctcaa tcaaagaatt acctcaggag tctatatgtg tgcagtagct     420
atagccctag gatacaaaga aatttatctt tctggaattg attttttatca aaatgggtca     480 tcttatgctt tgataccaa acaagaaaat cttttaaaac tggctcctga ttttaaaaat     540
gatcgctcac actatatcgg acatagtaaa aatacagata taaaagcttt agaatttcta     600
gaaaaaactt acaaaataaa actatattgc ttatgtccta acagtctttt agcaaatttt     660
```

```
atagaactag cgccaaattt aaattcaaat tttatcatac aagaaaaaaa taactacact    720
aaagatatac tcataccttc tagtgaggct tatggaaaat tttcaaaaaa tattaatttt    780
aaaaaaataa aaattaaaga aaatatttat tacaagttga taaaagatct attaagatta    840
cctagtgata taaagcatta tttcaaagga aaataa                              876
```

```
<210> SEQ ID NO 2
<211> LENGTH: 876
<212> TYPE: DNA
<213> ORGANISM: Campylobacter Jejuni
<220> FEATURE:
<223> OTHER INFORMATION: Campylobacter sialytransferases II (NCBI
      accession number AX934427)

<400> SEQUENCE: 2
atgaaaaaag ttattattgc tggaaatgga ccaagtttaa aagaaattga ttattcaagg     60
ctaccaaatg attttgatgt atttagatgc aatcaatttt attttgaaga taaatactat    120
cttggtaaaa aattcaaagc agtattttac aatcctggtc ttttttttga acaatactac    180 acttttaaaac atttaatcca aaatcaagaa tatgagaccg aactaattat gtgttctaat    240
tacaaccaag ctcatctaga aaatgaaaat tttgtaaaaa cttttttacga ttattttcct    300 gatgctcatt tgggatatga ttttttttaaa caacttaaag aatttaatgc ttattttaaa    360
tttcacgaaa tttatctcaa tcaaagaatt acctcaggag tctatatgtg tgcagtagct    420
atagccctag gatacaaaga aatttatctt tctggaattg attttttatca aaatgggtca    480 tcttatgctt ttgataccaa acaagaaaat cttttaaaac tggctcctga ttttaaaaat    540
gatcgctcac actatatcgg acatagtaaa aatacagata taaaagcttt agaatttcta    600
gaaaaaactt acaaaataaa actatattgc ttatgtccta acagtctttt agcaaatttt    660
atagaactag cgccaaattt aaattcaaat tttatcatac aagaaaaaaa taactacact    720
aaagatatac tcataccttc tagtgaggct tatggaaaat tttcaaaaaa tattaatttt    780
aaaaaaataa aaattaaaga aaatatttat tacaagttga taaaagatct attaagatta    840
cctagtgata taaagcatta tttcaaagga aaataa                              876
```

```
<210> SEQ ID NO 3
<211> LENGTH: 876
<212> TYPE: DNA
<213> ORGANISM: Campylobacter Jejuni
<220> FEATURE:
<223> OTHER INFORMATION: Campylobacter glycosyltransferases (NCBI
      accession number AR271702)

<400> SEQUENCE: 3
atgaaaaaag ttattattgc tggaaatgga ccaagtttaa aagaaattga ttattcaaga     60
ctaccaaatg attttgatgt atttagatgc aatcaatttt attttgaaga taaatactat    120
cttggtaaaa aatgcaaagc agtattttac aatcctagtc ttttttttga acaatactac    180 acttttaaaac atttaatcca aaatcaagaa tatgagaccg aactaatcat gtgttctaat    240
tttaaccaag ctcatctaga aaatcaaaat tttgtaaaaa cttttttacga ttattttcct    300 gatgctcatt tgggatatga ttttttcaaa caacttaaag aattcaatgc ttattttaaa    360
tttcacgaaa tttatttcaa tcaaagaatt acctcagggg tctatatgtg cacagtagcc    420
atagccctag gatacaaaga aatttatctt tcgggaattg attttttatca aaatggatca    480 tcttatgctt ttgataccaa acaaaaaaat cttttaaaat tggctcctaa ttttaaaaat    540
```

```
gataattcac actatatcgg acatagtaaa aatacagata taaaagcttt agaatttcta      600
gaaaaaactt acgaaataaa gctatattgt ttatgtccta acagtctttt agcaaatttt      660
atagaactag cgccaaattt aaattcaaat tttatcatac aagaaaaaaa taactatact      720
aaagatatac tcataccttc tagtgaggct tatggaaaat ttacaaaaaa tattaatttt      780
aaaaaaataa aaattaaaga aaatatttat tacaagttga taaaagatct attaagatta      840
cctagtgata taaagcatta tttcaaagga aaataa                                876

<210> SEQ ID NO 4
<211> LENGTH: 876
<212> TYPE: DNA
<213> ORGANISM: Campylobacter Jejuni
<220> FEATURE:
<223> OTHER INFORMATION: Campylobacter glycosyltransferases (NCBI
      accession number AX934429)

<400> SEQUENCE: 4
atgaaaaaag ttattattgc tggaaatgga ccaagtttaa aagaaattga ttattcaaga       60
ctaccaaatg attttgatgt atttagatgc aatcaatttt attttgaaga taaatactat      120
cttggtaaaa aatgcaaagc agtattttac aatcctagtc ttttttttga acaatactac      180
actttaaaac atttaatcca aaatcaagaa tatgagaccg aactaatcat gtgttctaat      240
tttaaccaag ctcatctaga aaatcaaaat tttgtaaaaa cttttttacga ttattttcct      300 gatgctcatt tgggatatga ttttttcaaa caacttaaag aattcaatgc ttattttaaa      360
tttcacgaaa tttatttcaa tcaaagaatt acctcagggg tctatatgtg cacagtagcc      420
atagccctag gatacaaaga aattatctt tcgggaattg atttttatca aaatggatca      480
tcttatgctt ttgataccaa acaaaaaaat cttttaaaat tggctcctaa ttttaaaaat      540
gataattcac actatatcgg acatagtaaa aatacagata taaaagcttt agaatttcta      600
gaaaaaactt acgaaataaa gctatattgt ttatgtccta acagtctttt agcaaatttt      660
atagaactag cgccaaattt aaattcaaat tttatcatac aagaaaaaaa taactatact      720
aaagatatac tcataccttc tagtgaggct tatggaaaat ttacaaaaaa tattaatttt      780
aaaaaaataa aaattaaaga aaatatttat tacaagttga taaaagatct attaagatta      840
cctagtgata taaagcatta tttcaaagga aaataa                                876
```